(12) United States Patent
Young et al.

(10) Patent No.: US 9,180,264 B2
(45) Date of Patent: Nov. 10, 2015

(54) MEDICATED MODULE FOR AN INHALER (75) Inventors: Alasdair George Young, Oxfordshire (GB); Daniel Thomas De Sausmarez Lintell, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 251 days.

(21) Appl. No.: 13/989,028

(22) PCT Filed: Nov. 28, 2011

(86) PCT No.: PCT/EP2011/071118
§ 371 (c)(1),
(2), (4) Date: May 22, 2013

(87) PCT Pub. No.: WO2012/072542
PCT Pub. Date: Jun. 7, 2012

(65) Prior Publication Data
US 2013/0239964 A1    Sep. 19, 2013

Related U.S. Application Data

(60) Provisional application No. 61/433,696, filed on Jan. 18, 2011.

(30) Foreign Application Priority Data

Nov. 29, 2010   (EP) .................................... 10192975

(51) Int. Cl.
*A61M 15/00*    (2006.01)
(52) U.S. Cl.
CPC ............ *A61M 15/00* (2013.01); *A61M 15/0003* (2014.02); *A61M 15/009* (2013.01);
(Continued)

(58) Field of Classification Search
CPC ............ A61M 15/00; A61M 15/0001; A61M 15/0003; A61M 15/0005; A61M 15/0021; A61M 15/0025; A61M 15/0028; A61M 15/003; A61M 15/0033; A61M 15/0035; A61M 15/0036; A61M 15/004; A61M 15/0041; A61M 15/0043; A61M 15/0061; A61M 15/0063; A61M 15/0065; A61M 15/0086; A61M 15/009; A61M 2202/064
USPC ............ 128/200.14, 200.19, 200.21, 200.23, 128/203.12, 203.15, 203.21, 203.23
See application file for complete search history.

(56) References Cited

U.S. PATENT DOCUMENTS 1,789,921 A * 1/1931 Adam ...................... 128/203.23
5,002,048 A * 3/1991 Makiej, Jr. ............... 128/200.23
(Continued)

FOREIGN PATENT DOCUMENTS

GB       2253200 A *  9/1992  ................ A61J 1/06
WO  WO 02074360 A2 *  9/2002
(Continued)

OTHER PUBLICATIONS

International Preliminary Report on Patentability mailed Jun. 13, 2013 in International Application No. PCT/EP2011/071118.

*Primary Examiner* — Lynne Anderson
*Assistant Examiner* — Joseph D Boecker
(74) *Attorney, Agent, or Firm* — McDonnell Boehnen Hulbert & Berghoff LLP (57) ABSTRACT

A medicated module containing a medicament is configured for removable attachment to the mouthpiece of an inhaler. The inhaler may contain a first medicament such that a single firing of the inhaler will deliver both medicaments to the user.

12 Claims, 3 Drawing Sheets

(52) U.S. Cl.
CPC ....... *A61M15/0025* (2014.02); *A61M 15/0028* (2013.01); *A61M 15/0036* (2014.02); *A61M 15/0041* (2014.02); *A61M 15/0063* (2014.02); *A61M 15/0086* (2013.01)

(56) References Cited

U.S. PATENT DOCUMENTS

| | | | | |
|---|---|---|---|---|
| 5,522,380 | A * | 6/1996 | Dwork | 128/200.23 |
| 6,655,381 | B2 * | 12/2003 | Keane et al. | 128/203.15 |
| 7,029,465 | B2 * | 4/2006 | Heyes et al. | 604/406 |
| 7,954,486 | B2 * | 6/2011 | Papania et al. | 128/200.14 |
| 8,800,554 | B2 * | 8/2014 | Gordon et al. | 128/203.15 |
| 2002/0020408 | A1 | 2/2002 | Knauer | |
| 2003/0015191 | A1 | 1/2003 | Armstrong et al. | |
| 2003/0178024 | A1 * | 9/2003 | Allan et al. | 128/200.24 |
| 2004/0227011 | A1 | 11/2004 | Tseng | |
| 2005/0028813 | A1 * | 2/2005 | Harrison | 128/200.22 |
| 2005/0154491 | A1 * | 7/2005 | Anderson et al. | 700/236 |
| 2005/0252508 | A1 * | 11/2005 | Koerner et al. | 128/200.14 |
| 2005/0258273 | A1 | 11/2005 | Bruna et al. | |
| 2005/0274378 | A1 * | 12/2005 | Bonney et al. | 128/200.23 |
| 2006/0000473 | A1 * | 1/2006 | Myrman | 128/203.15 |
| 2008/0163869 | A1 * | 7/2008 | Nobutani et al. | 128/200.23 |
| 2010/0186738 | A1 * | 7/2010 | Kobayashi et al. | 128/200.14 |
| 2013/0206142 | A1 * | 8/2013 | Dudley et al. | 128/203.15 |

FOREIGN PATENT DOCUMENTS

| | | | |
|---|---|---|---|
| WO | WO 2008091355 | A2 * | 7/2008 |
| WO | 2009014153 | A1 | 1/2009 |

* cited by examiner

MEDICATED MODULE FOR AN INHALER

CROSS REFERENCE TO RELATED APPLICATIONS

The present application is a U.S. National Phase Application pursuant to 35 U.S.C. §371 of International Application No. PCT/EP2011/071118 filed Nov. 28, 2011, which claims priority to European Patent Application No. 10192975.0 filed Nov. 29, 2010 and U.S. Provisional Patent Application No. 61/433,696 filed Jan. 18, 2011. The entire disclosure contents of these applications are herewith incorporated by reference into the present application.

FIELD OF INVENTION

The present application relates to medical devices for delivering one or more drug using inhaler devices. Especially, the present application relates to medical devices and methods of delivering at least two drug agents from separate reservoirs using inhaler devices having only a single activation mechanism, button or trigger and a single dispense interface (i.e. a mouthpiece). A delivery procedure initiated by the user causes a non-user settable dose (i.e., a fixed dose) of a second drug agent along with a set dose of a first drug agent to be delivered to the patient. The drug agents may be available in two or more reservoirs, containers, or packages, each containing independent (single drug compound) or pre-mixed (co-formulated multiple drug compounds) drug agents.

BACKGROUND

Certain diseases or require treatment of many patients with a same or similar dose of medicament. The medicaments or drug compounds need to be delivered in a fast, secure and cost effective way. This invention is of particular benefit where the therapy requires oral application of a medicament.

This invention is beneficial where one or more drugs need to be delivered for inhalation, especially when a sterile medicament shall be given to one or more patients with a single inhaler device.

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance, and/or toxicology.

For example, in some cases it might be beneficial to treat a person suffering from diabetes with a combination of a long acting insulin along with a glucagon-like peptide-1 (GLP-1). This GLP-1 is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. Alternatively, other combination of drugs such as those to treat asthma, e.g., LABA (Long acting beta agonists) and Cortico-steroids could be used in this invention.

The term "drug" or "medicament", as used herein, means a pharmaceutical formulation containing at least one pharmaceutically active compound, for example for the treatment of obstructive airway or lung diseases such as asthma or chronic obstructive pulmonary disease (COPD), allergies, diabetes mellitus.

The active pharmaceutical compound is preferably selected from the group consisting of active pharmaceutical compounds suitable for inhalation, preferably antiallergenic, antihistamine, anti-inflammatory, antitussive agents, bronchodilators, anticholinergic drugs, and combinations thereof.

The active pharmaceutical compound may for example be chosen from:

an insulin such as human insulin, e.g. a recombinant human insulin, or a human insulin analogue or derivative, a glucagon-like peptide (GLP-1) or an analogue or derivative thereof, or exendin-3 or exendin-4 or an analogue or derivative of exendin-3 or exendin-4;

an adrenergic agent such as a short acting β2-agonists (e.g. Salbutamol, Albuterol, Levosalbutamol, Fenoterol, Terbutaline, Pirbuterol, Procaterol, Bitolterol, Rimiterol, Carbuterol, Tulobuterol, Reproterol), a long acting β2-agonist (LABA, e.g. Arformoterol, Bambuterol, Clenbuterol, Formoterol, Salmeterol), an ultra LABA (e.g. Indacaterol) or another adrenergic agent (e.g. Epinephrine, Hexoprenaline, Isoprenaline (Isoproterenol), Orciprenaline (Metaproterenol));

a glucocorticoid (e.g. Beclometasone, Budesonide, Ciclesonide, Fluticasone, Mometasone, Flunisolide, Betamethasone, Triamcinolone);

an anticholinergic agent or muscarinic antagonist (e.g. Ipratropium bromide, Oxitropium bromide, Tiotropium bromide);

a mast cell stabilizer (e.g. Cromoglicate, Nedocromil);

a xanthine derivative (e.g. Doxofylline, Enprofylline, Theobromine, Theophylline, Aminophylline, Choline theophyllinate);

an eicosanoid inhibitor, such as a leukotriene antagonist (e.g. Montelukast, Pranlukast, Zafirlukast), a lipoxygenase inhibitor (e.g. Zileuton) or a thromboxane receptor antagonist (e.g. Ramatroban, Seratrodast);

or a combination of any two, three or more of the above-mentioned compound classes or compounds (e.g. Budesonide/Formoterol, Fluticasone/Salmeterol, Ipratropium bromide/Salbutamol, Mometasone/Formoterol);

or a pharmaceutically acceptable salt or solvate or esters of any of the above named compounds Pharmaceutically acceptable salts are for example acid addition salts and basic salts. Acid addition salts are e.g. a chloride, bromide, iodide, nitrate, carbonate, sulfate, methylsulfate, phosphate, acetate, benzoate, benzenesulfonate, fumarate, malonate, tartrate, succinate, citrate, lactate, gluconate, glutamate, edetate, mesylate, pamoate, pantothenate or a hydroxy-naphthoate salt. Basic salts are for example salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology. Pharmaceutically acceptable ester may for example be acetates, propionates, phosphates, succinates or etabonates.

Pharmaceutically acceptable solvates are for example hydrates.

A number of potential problems can arise when delivering two active medicaments or "agents" simultaneously. As just one example, the two active agents when present in a single container may interact with each other during the long-term, shelf life storage of the formulation. Therefore, there are certain advantages to storing the active components separately and then potentially combine them at the point of delivery, e.g. injection, needle-less injection, pumps, or inhalation. However, any potential process for combining the two or more agents needs to be straightforward and convenient for the user to perform reliably, repeatedly, and safely.

One further concern is that the quantities and/or proportions of each active agent making up the potential combination dose or therapy may need to be varied for each user or at different stages of their therapy. Again, as just one example, one or more active agents may require a titration period to gradually introduce a patient to a "maintenance" dose. A further example would be if one active agent requires a non-adjustable fixed dose while the other agent is varied in response to a patient's symptoms or physical condition. This potential concern could mean that pre-mixed formulations of multiple active agents may not be suitable as these pre-mixed formulations would have a fixed ratio of the active components, which could not be varied by the healthcare professional or user.

Additional concerns may arise where a multi-drug compound therapy is required, because certain users may not be able to cope with having to use more than one drug delivery system or make the necessary accurate calculation of the required dose combination. This is especially true for users with dexterity or computational difficulties.

Accordingly, there exists a strong need to provide devices and methods for the delivery of two or more medicaments in a single activation of an inhaler-type drug delivery device, such a pressurized metered dose inhaler that is simple and safe for the user to perform and that also tends to reduce a patient's anxiety towards taking repeated doses of medicaments.

SUMMARY

The present application discloses a medicated module attachable to an inhaler device, preferably one containing a pressurized canister of multi-doses propellant, for example a so-called pressurized metered dose inhaler (pMDI) device. According to one aspect of the invention the pressurized canister may contain multi-doses of a primary or first medicament. The medicated module of this invention provides a means by which the user is able to receive doses of two medicaments from a single activation of the primary device thus reducing their burden on storage and complexity of operation. The medicated module seeks to maintain the plume geometry profile of the primary device by ensuring that the geometry of the outlet orifice relative to the mouthpiece of the medicated module is the same as that of a standard pMDI. Maintenance of such design geometry should help to ensure good comparability between medicament delivery of the first medicament from the primary device when used in isolation, as well as when it is combined with the medicated module.

According to another aspect of the invention, the medicated module of this invention provides a means by which the user is able to receive a single dose of medicament from a sterile container. The inhaler device may have a pressurized canister containing propellant. The medicated module may comprise a single dose of medicament. Each dose is separately contained in the medicated module and is sterile up until the point of administration. Hence, the medicament is provided by the module rather than the inhaler device. By means of such a medicated module several users may benefit from sterile medication using the same inhaler device. For example, an inhaler mouthpiece may comprise the medicated module. Providing a new mouthpiece for each patient can help care givers, e.g., in donating each patient a safe and sterile oral medication. Along with the ease of use it is understood that this solution is also cost efficient, while maintaining high quality medical standards.

Prior to use, i.e., attachment to an inhaler, the medicated module provides a means of containing a medicament within a sealed drug cavity or reservoir. Potential materials that might be used to form the drug cavity that holds the second medicament might include (but are not limited to); Acetal (polyoxymethylene, polyacetal or polyformaldehyde), COC (Cyclo Olefin Copolymer), COP (Cyclo Olefin Polymer) and PBT (Polybutylene Terephthalate). Sealing of the reservoir in the medicated module may be achieved through a combination of foil seals (single or multi-layer), stopper bungs, septa or like means known in the art.

On assembly to the primary or inhaler device, the reservoir in the medicated module is automatically engaged thus establishing the flow path to the outlet spray orifice, i.e., mouthpiece, at the distal end of the medicated module. Preferably, connections in the flow path could be established using a compliant material, such as rubber or TPE, to help ensure minimal or no leakage occurs during dispense and thus delivered dose performance is maintained. The act of engaging the fluid path of the reservoir with that of the canister in the inhaler automatically during assembly simplifies the users interaction with the device.

The system may also be configured to help ensure that the medicated module is only capable of being used once by a user. This may be achieved through integration of a mechanical flap (or similar airflow restriction means) that is only activated (closed off) following an inhalation by a user through the device. The aim of any such mechanism or feature would be to prevent/significantly restrict subsequent further airflow through the medicated module, thereby alerting a user to this situation. Alternatively and/or additionally our invention could include features to;

1. Prevent re-attachment of a previously used medicated module to the primary drug delivery or inhaler device.
2. Prevent removal of the replaceable mouthpiece cap of the medicated module following use and replacement.
3. Physical blocking of the axial movement of the canister in the primary or inhaler device.
4. Visual warnings (e.g. warning text/indicia within an indication window on the module) once dosing has occurred.

In one embodiment of the invention the medicated module for use with a drug inhaler includes a housing configured for removable attachment to the mouthpiece of the inhaler, where the housing has a distal end and a proximal end. There is at least one reservoir contained within the housing having at least one dose of medicament, where the reservoir has a first seal and a second seal. A cannula or other type of flow path is mounted in the proximal end of the housing such that when the module is attached to the mouthpiece of the inhaler, preferably by insertion into the mouthpiece, the first seal is pierced by the cannula to establish fluid communication with the output from the primary reservoir or canister of the inhaler.

Alternatively, the flow path is reversibly closed by a check valve acting as the first seal. A protrusion at the proximal end of the housing of the module may be configured to open the seal when the module is attached. For example, the first seal may comprise a ball biased by a spring in a sealing position. When the module is attached the protrusion engages with the ball and moves it against the biasing force thus opening a flow path. The seal is in an open position. Upon removing the module from the inhaler, the ball returns to its first position due to the biasing force and the seal is closed again. Other types of check valve or back-flow valve are also feasible. As a further alternative, the first seal may comprises shear pin protruding the proximal end of the housing of the module. The shear pin may sealingly close the flow path to the reservoir. When the module is attached to the inhaler device the shear pin may engage with an inner part of the inhaler and, due to its construction, may break away and the first seal is open.

In a further embodiment, the medicated module has a removable cap connected to the distal end. Preferably the cap is operatively connected to the second seal such that removal of the cap removes the second seal from reservoir. The cap also maintains the interior chamber of the medicated module sterile until immediately prior to use.

Although the reservoir of the medicated module can be designed in a number of configurations and orientations, two preferred configurations include one that is inline with the axis of the mouthpiece (or axis of the cannula) and other oriented at approximately 90 degrees to the axis of the mouthpiece. This latter configuration is a venturi design whereby the flow of the first medicament or fluid from the primary reservoir or canister in the inhaler causes the second medicament in the medicated module reservoir to be drawn into the flowing stream of first medicament or fluid. In some instances it might be desirable to include a slider or other movable piece on the medicated module such that the user can remove an internal seal associated with the reservoir.

In a further embodiment the medicated module may further comprise a reservoir activation mechanism, wherein the reservoir activation mechanism is movable from a first status when the medicated module is not in an attached condition to a second status when the medicated module is in an attached condition. When the reservoir activation mechanism is in the first status the reservoir of the medicated module is not in fluid communication with a flow path of the inhaler device. When the reservoir activation mechanism is in the second status the reservoir of the medicated module is in fluid communication with a flow path of the inhaler device.

In a further embodiment the medicated module may further comprise a reservoir activation mechanism, wherein the reservoir activation mechanism is movable relative to the housing from a first position when the medicated module is not in an attached condition to a second position when the medicated module is in an attached condition.

In a further embodiment the medicated module may comprise a reservoir activation mechanism which is configured for engaging and forming a sealed flow path with a channel on the drug inhaler when in the attached condition.

In a further embodiment the reservoir activation mechanism may comprise a flow path, a biasing element, and a gasket, wherein the flow path is configured to establish fluid communication between the reservoir of the medicated module and a channel on the drug inhaler when the medicated module is in attached condition.

In a further embodiment of the medicated module may comprise a reservoir activation mechanism wherein the flow path comprises a cannula, the biasing element comprises a spring and when the medicated module is in the attached condition the reservoir activation mechanism is in the second position against a force exerted by the spring, the seal is pierced by the cannula, and the gasket is compressed to form a seal with the channel on the drug inhaler.

Another aspect of the invention relates to a system of one or more of the previously described medicated modules in combination with an inhaler comprising a propellant. According to an embodiment the inhaler may comprise a pressurized meter dose inhaler (pMDI). In a further embodiment the inhaler may comprise a propellant and at least one medicament.

In yet another embodiment, the invention comprises a system of one or more of the previously described medicated modules in combination with an inhaler containing a primary medicament, preferably a pressurized meter dose inhaler (pMDI).

In a preferred embodiment a master drug compound, such as insulin, contained within a multiple dose, user-selectable device could be used with a single use, user-replaceable, module that contains a single dose of a secondary medicament, such as GLP-1 and the single dispense interface. When connected to the drug delivery device the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
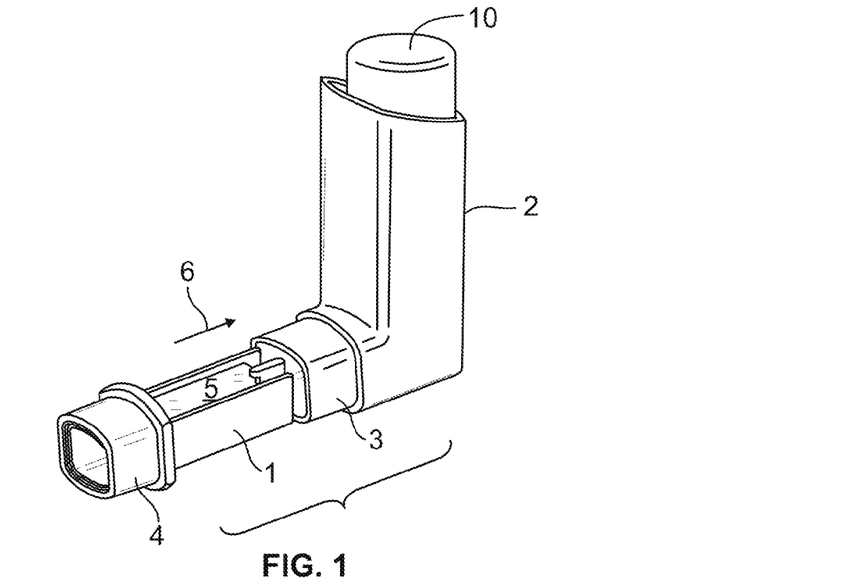
FIG. 1 illustrates a perspective view of one possible drug delivery system of the present invention where a medicated module according to the present invention is shown being inserted into the mouthpiece of an inhaler.

The presently proposed medicated module may be used with an inhaler-type drug delivery device, such as the inhaler 2 illustrated in FIG. 1. In one arrangement, the presently proposed medicated module administers one or more single doses of a second medicament simultaneously with a fixed dose of a first medicament from a multi-dose reservoir within the inhaler through a single output or drug dispense interface such as module mouthpiece 11. A single activation of inhaler 2, for example by pushing container 10 down in a vertically direction 50, will cause both the first and second medicaments to be delivered to the user. The volume and size of the dose of the second medicament is independently controlled by the design and manufacture of the reservoir in the medicated module and therefore not influenced by the size of the dose generated by the inhaler during activation. This fixed dose of the second medicament contained within the medicated module may be a single dose.

In another arrangement, the presently proposed medicated module administers one single dose of medicament from the medicated module simultaneously with a propellant from a multi-dose reservoir or canister or container within the inhaler 2 through a single output or drug dispense interface such as module mouthpiece 11. A single activation of inhaler 2, for example by pushing container 10 down in a vertically direction 50, will cause the propellant together with the medicament to be delivered to the user. The volume and size of the dose of the medicament is independently controlled by the design and manufacture of the reservoir in the medicated module and therefore not influenced by the size of the dose generated by the inhaler during activation. This fixed dose of the medicament contained within the medicated module may be a single dose.

The construction and design of the medicated module 1 according to the invention as well as the method of use and operation is irrelevant of the fact, whether the inhaler device 2 comprises a first medicament or simply a propellant. Hence, details regarding the construction and design as well as the method of use and operation apply to both embodiments. For simplicity and readability only differences—if any—are explicitly mentioned. However, one skilled in the art will immediately understand and capture the essence of the description leaving no doubt that certain features described in the context of one embodiment will apply the same way to other embodiments without change.

Figure 2:
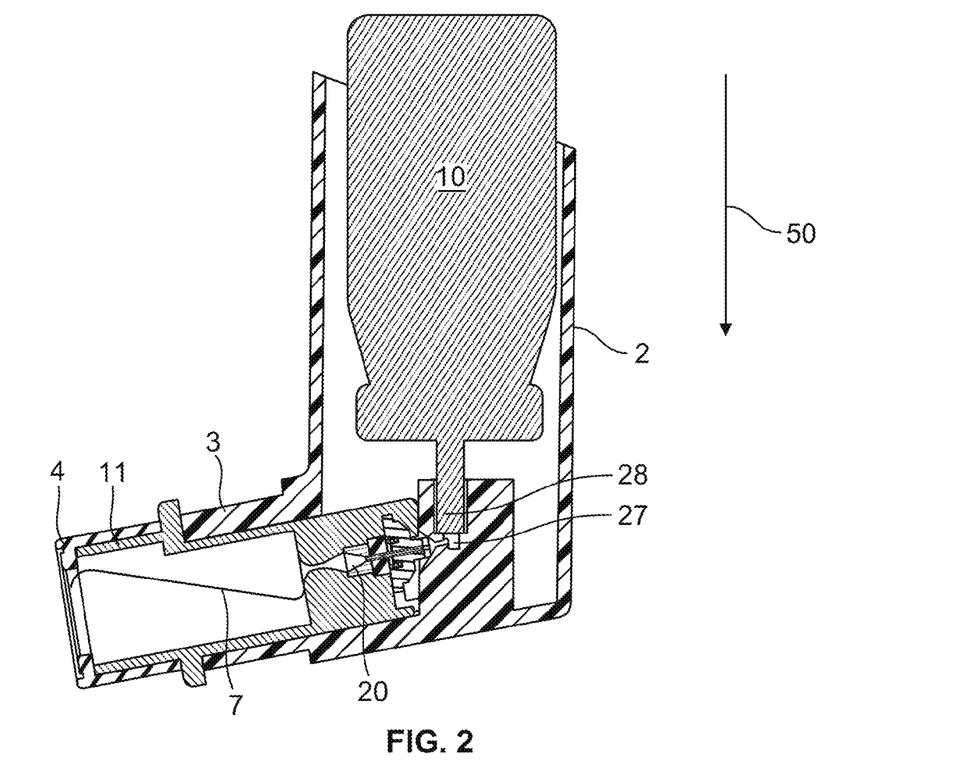
FIG. 2 illustrates a sectional view of one arrangement of a medicated module attached to an inhaler.
Figure 5:
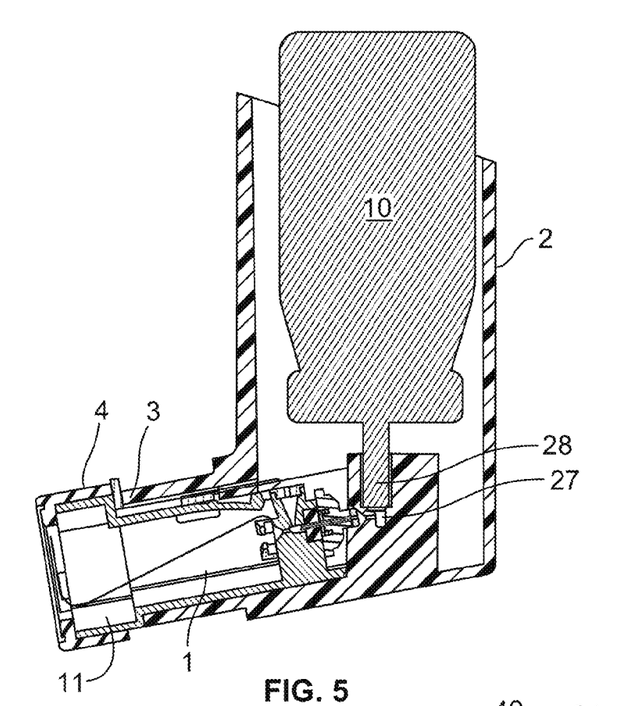
FIG. 5 illustrates a sectional view of another embodiment of a medicated module of the present invention attached to an inhaler.
Figure 6:
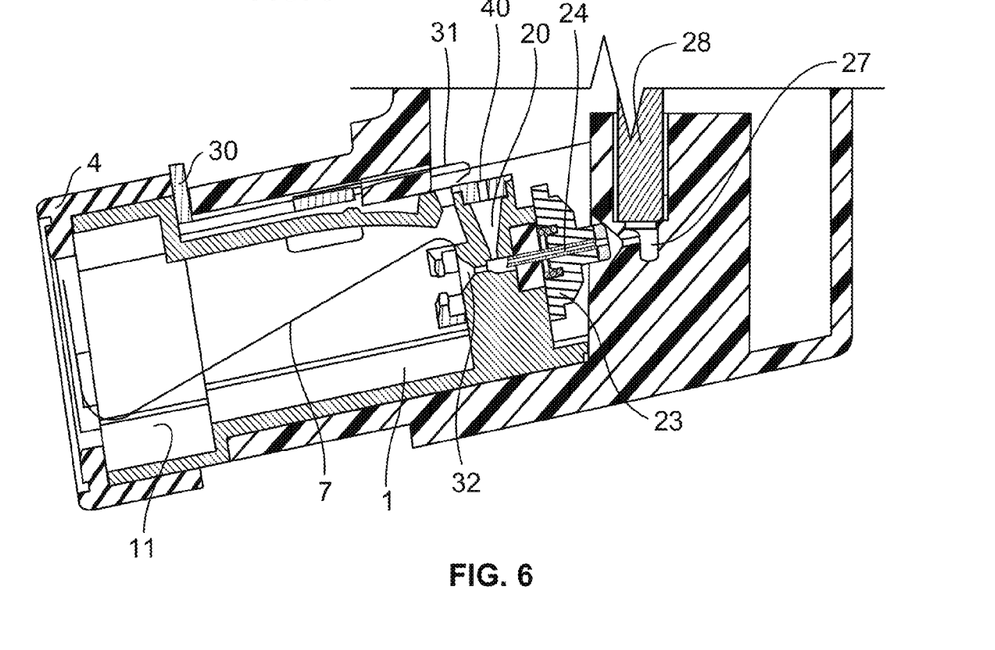
FIG. 6 illustrates a sectional view of the medicated module illustrated in FIG. 5 after attachment to the mouthpiece of the inhaler.

In a preferred arrangement, the drug dispense interface comprises a module mouthpiece, such as the mouthpiece 11 shown in FIGS. 2, 5 and 6, however, any channel or flow path capable of passing a spray or aerosol could be used. As shown in FIG. 1, the medicated module 1 comprising a housing 5 that is preferably designed and configured to be removably attached in direction 6 to a standard inhaler 2. A preferred attachment is one where the housing 5 of the medicated module 1 can be inserted into the mouthpiece 3 of the inhaler 2. The housing 5 is held in place using any reversible connection means known to the art, for example, threads, snap locks, snap fits, detents, luer locks, bayonet, snap rings, keyed slots, and combinations of such connections. Preferably, the attachment mechanism between the medicated module and the inhaler is configured such that the user can easily attach the module to the inhaler and then easily remove the module after expelling the second medicament contained in the module. In certain applications, the connector or attachment configuration may comprise an exclusive attachment where such an exclusive attachment would only allow such a medicated module to be attached to only certain types of inhaler drug delivery devices and prevented from being attached to other types of inhalers or other drug delivery devices. Once the module is removed, the inhaler can then be used as a stand-alone drug delivery device to administer the first or primary medicament.

Although the inhaler device 2 shown in the figures is a pressured metered dose inhaler (pMDI) holding a replaceable pressurized canister 10 containing multiple doses of a first medicament, alternative types of inhalation device can be used with the present invention. As mentioned before, an alternative type of inhalation device could comprise a pressured metered dose inhaler (pMDI) holding a replaceable pressurized canister 10 containing a propellant without a first medicament.

Figure 3:
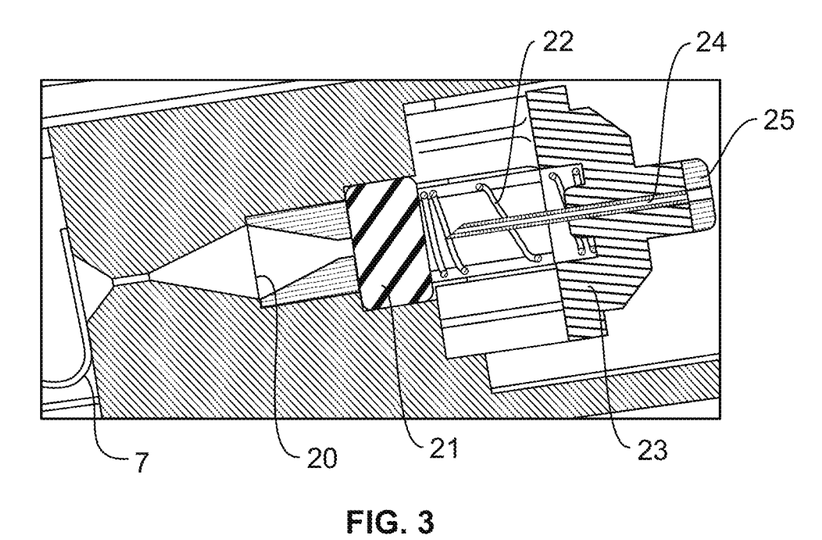
FIG. 3 illustrates a sectional view of the medicated module illustrated in FIG. 2 prior to attachment to the mouthpiece of the inhaler.
Figure 4:
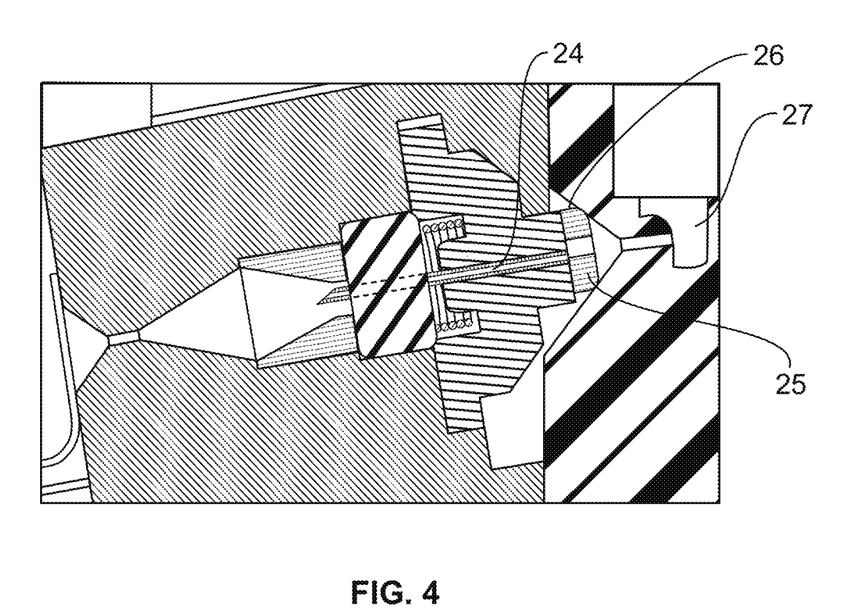
FIG. 4 illustrates a sectional view of the medicated module illustrated in FIG. 2 after attachment to the mouthpiece of the inhaler.

Referring now to FIGS. 3 and 4, these figures show a close-up view of the cross-sectional view of the medicated module 1, focusing specifically on reservoir 20 that holds the second medicament and the reservoir activation mechanism 23. The reservoir 20 is sealed at the proximal end by a first seal 21 and at the distal end by removable second seal 7. The reservoir activation mechanism 23 contains a cannula 24 or other flow path, a biasing element 22, and a gasket 25 for engaging and forming a sealed flow path with channel 27 on inhaler 2. FIG. 3 shows the activation mechanism 23 prior to attachment of the module to the inhaler. Seal 7 remains attached and cannula 24 has not pierced seal 21 because biasing element 22, preferably a spring, exerts a force in the distal direction. FIG. 4 shows the activation mechanism after the module 1 is attached to inhaler 2. Once attached, the activation mechanism is pushed axially in the distal direction thus compressing biasing element 22 and allowing cannula 24 to pierce seal 21 and become in fluid communication with reservoir 20. Likewise, gasket 25 is compressed to form a seal with wall 26 of channel 27 to provide fluid communication with the proximal end of cannula 24.

Once the medicated module is attached, as indicated by directional arrow 6 (see FIG. 1), the user can remove outer cap 4 from the module and because the cap is connected to a portion of the second seal 7, this will cause seal 7 to peel or tear away from the distal end of reservoir 20. Removing seal 7 now places the reservoir and the second medicament contained therein in fluid communication with module mouthpiece 11.

The user operates the combination of medicated module 1 and inhaler 2 in exactly the same manner as they would if the module was not attached. The user would place module mouthpiece 11 into the mouth and then press vertically down on canister 10 while inhaling through the system. This single activation of the system causes a single dose of the first medicament to exit orifice 28 of canister 10, which then travels through channel 27 into cannula 24 and into reservoir 20. The pressurized first medicament provides the driving force to expel the second medicament contained in reservoir 20 out of the module through mouthpiece 11. Depending on the design of the reservoir and/or the properties of the medicaments, the first medicament may be expelled with the second medicament as a mixture or may be expelled sequentially.

Preferably, in the embodiment shown in FIGS. 1-4, the reservoir is positioned along the axis of the mouthpieces 3 and 11 and along the axis of cannula 24. In another alternative embodiment, the reservoir can be positioned at an angle relative to these axes, for example the reservoir can be positioned within the housing at an angle in the range from about 60 to 120 degrees measured relative to an axis defined by the cannula, preferably normal or at 90 degrees. In one preferred arrangement, the reservoir comprises a single dose of the second medicament, such as a single dose of an active agent such as GLP-1. Alternatively, the reservoir comprises a single dose of a premix of active agents or medicaments. In one preferred arrangement, this primary medicament comprises a different type of medicament as the medicament contained within the drug delivery device.

Alternatively, in the embodiment shown in FIGS. 1-4, the inhaler 2 comprises a canister or container with a propellant, but without medicament. The user operates the combination of medicated module 1 and inhaler 2 in exactly the same manner as described above. The user places module mouthpiece 11 into the mouth and then press vertically down on canister 10 while inhaling through the system. This single activation of the system causes a single dose of propellant to exit orifice 28 of canister 10, which then travels through channel 27 into cannula 24 and into reservoir 20. The pressurized propellant provides the driving force to expel the medicament contained in reservoir 20 out of the module through mouthpiece 11.

One example of the alternative positioning of reservoir 20 is illustrated in FIGS. 5 and 6, where the reservoir is at an angle in the range of from about 60 to about 120 degrees, preferably substantially 90 degree vertical position relative to the cannula 24 or flow path through the mouthpieces. In this position the reservoir and cannula cooperate as a venturi mechanism, preferably a venturi injector whereby fluid passing through the cannula into reservoir chamber 32 draws in fluid contained in the reservoir. In this embodiment a third seal (not shown) is attached to the top portion 40 of reservoir 20. This seal is preferably attached to slider opener 31 and is removed by slider opener 31 when slider 30 is activated by the attachment of medicated module 1 to inhaler 2. As the medicated module is pushed into the inhaler slider 30 is moved in the opposite (distal) direction causing slider opener 31 to tear or peel away the third seal located at position 40.

As with the previously described embodiment, removal of cap 4 pulls off seal 7 from the distal end of the reservoir chamber 32. Activation mechanism 23 is also triggered by attachment of the medicated module in the manner as described above. The reservoir 20 is now in fluid communication with channel 27 of inhaler 2 and mouthpiece 11. A single activation of the inhaler will cause a dose of the first medicament to exit canister 10, flow through exit 28 and channel 27, through cannula 24, past the distal end of reservoir 20 drawing into the cannula the second medicament and discharging both medicaments into mouthpiece 11 and eventually administered to the user. In such an arrangement the system may be preferably configured to prevent the risk of any back-flow into or through the reservoir of secondary medicament contained in the medicated module.

It is within the scope of the invention to configure the medicated module with a locking mechanism so as to lock and/or block the distal end, proximal end, or both after dose administration. One advantage of locking the medicated module from repeated use is that a user will be prevented from reusing an expended medicated module and therefore eliminate the possibility that a user would use the expended medicated module under the assumption that he or she is receiving the predefined dose of the secondary medicament stored in a new medicated module. Likewise, such a blocking/locking feature prevents a user from re-using a non-sterile medicated module after a dose has been delivered.

The medicated module arrangements herein disclosed are preferably self-contained and may be provided as a sealed and sterile disposable module. Although not shown, the medicated modules disclosed herein could be supplied by a manufacturer contained in a protective and sterile capsule or container where the user would peel or rip open a seal or the container itself to gain access to the sterile medicated module. In some instances it might be desirable to provide two or more seals for each end of the medicated module.

Moreover, in the arrangements discussed above, these arrangements have the benefit in that the second medicament is contained entirely within the medicated module, separate and away from the first medicament contained within the inhaler-type drug delivery device.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module configured for use with a drug inhaler, the medicated module comprising: a housing configured for removable attachment to the drug inhaler, where the housing has a distal end and a proximal end; a removable cap; a reservoir containing a dose of medicament, where the reservoir has a first seal and a second seal; wherein the first seal is configured to be opened by attachment of the medicated module to the drug inhaler; and wherein the cap is operatively connected to the second seal such that removal of the cap removes the second seal from the reservoir.

2. The medicated module of claim 1 further comprising a cannula mounted in the proximal end of the housing, wherein the cannula is configured to pierce the first seal by attachment of the medicated module to a drug inhaler.

3. The medicated module of claim 1 further comprising a mouthpiece at the distal end of the housing.

4. The medicated module of claim 1 where the reservoir is positioned within the housing at an angle in the range of from about 60 to 120 degrees measured relative to an axis defined by a cannula so that the medicament from reservoir is drawn into a reservoir chamber.

5. The medicated module of claim 1 where the reservoir is configured as a venturi injector.

6. The medicated module of claim 1 further comprising a slider for opening a third seal connected to the reservoir when the slider is moved in a distal direction.

7. The medicated module of claim 1 further comprising a reservoir activation mechanism, wherein the reservoir activation mechanism is movable relative to the housing from a first position when the medicated module is not in an attached condition to a second position when the medicated module is in the attached condition.

8. The medicated module of claim 7 wherein the reservoir activation mechanism is configured for engaging and forming a sealed flow path with a channel on the drug inhaler when in the attached condition.

9. The medicated module of claim 7 where the reservoir activation mechanism comprises a flow path, a biasing element, and a gasket, wherein the flow path is configured to establish fluid communication between the reservoir and the channel on the drug inhaler when the medicated module is in the attached condition.

10. The medicated module of claim 9 wherein the flow path comprises a cannula, the biasing element comprises a spring and when the medicated module is in the attached condition the reservoir activation mechanism is in the second position against a force exerted by the spring, the first seal is pierced by the cannula, and the gasket is compressed to form a seal with the channel on the drug inhaler.

11. An inhaler drug delivery system comprising, in combination, the medicated module of claim 1; and a pressurized metered dose housing comprising a reservoir of compressed fluid.

12. An inhaler drug delivery system according to claim 11 wherein the reservoir of compressed fluid further comprises medicament.

* * * * *